(12) United States Patent
Menon (10) Patent No.: US 8,452,362 B2
(45) Date of Patent: *May 28, 2013

(54) METHOD AND SYSTEM FOR MONITORING HYDRATION

(75) Inventor: Naresh Menon, Pasadena, CA (US)

(73) Assignee: Chromologic LLC, Pasadena, CA (US)

( * ) Notice: Subject to any disclaimer, the term of this patent is extended or adjusted under 35 U.S.C. 154(b) by 488 days.

This patent is subject to a terminal disclaimer.

(21) Appl. No.: 12/694,187

(22) Filed: Jan. 26, 2010

(65) Prior Publication Data

US 2011/0184261 A1    Jul. 28, 2011

(51) Int. Cl.
*A61B 5/00* (2006.01)

(52) U.S. Cl.
USPC ........................... 600/318; 351/205

(58) Field of Classification Search
USPC ............... 600/310, 318, 558, 561; 351/205
See application file for complete search history.

(56) References Cited

U.S. PATENT DOCUMENTS

| | | | |
|---|---|---|---|
| 3,958,560 A | 5/1976 | March | |
| 3,963,019 A | 6/1976 | Quandt | |
| 4,166,695 A | 9/1979 | Hill et al. | |
| 4,836,207 A | 6/1989 | Bursell et al. | |
| 5,433,197 A | 7/1995 | Stark | |
| 6,611,704 B1 | 8/2003 | van Best et al. | |
| 6,721,583 B1 | 4/2004 | Durkin et al. | |
| 7,039,446 B2 | 5/2006 | Ruchti et al. | |
| 7,308,293 B2 | 12/2007 | Gerlitz | |
| 7,627,357 B2 | 12/2009 | Zribi et al. | |
| 2001/0029323 A1 | 10/2001 | Madarasz et al. | |
| 2001/0031914 A1* | 10/2001 | Gobeli et al. | 600/318 |
| 2003/0127609 A1 | 7/2003 | El-Hage et al. | |
| 2003/0233036 A1 | 12/2003 | Ansari et al. | |
| 2004/0147820 A1* | 7/2004 | Routt et al. | 600/318 |
| 2006/0258918 A1* | 11/2006 | Burd et al. | 600/310 |
| 2007/0078308 A1 | 4/2007 | Daly | |
| 2010/0249548 A1* | 9/2010 | Muller | 600/318 |
| 2011/0184262 A1* | 7/2011 | Menon | 600/318 |
| 2012/0041552 A1* | 2/2012 | Chuck et al. | 600/318 |

OTHER PUBLICATIONS

International Search Report, dated Mar. 30, 2010, for corresponding application No. PCT/US2010/022899, 2 pages.
Written Opinion of the International Searching Authority dated Mar. 30, 2010, for corresponding application No. PCT/2010/022899, 5 pages.
Cheuvront, Ph.D., et al., *Hydration Assessment of Athletes*, Sports Science Exchange, vol. 18, 2005, No. 2, 6 pages, 2005.
*Hydration Assessment of Athletes "WUT" Is the Answer?*, Sports Science Exchange, 2005, vol. 18, No. 2, 2 pages, 2005.

(Continued)

*Primary Examiner* — Christopher Mahoney
(74) *Attorney, Agent, or Firm* — Christie, Parker & Hale, LLP (57) ABSTRACT

A device for measuring a hydration status based on an analyte concentration in a subject. The device includes: a light source configured for illuminating at least a portion of an anterior region of an eye of the subject with incident light having a substantially broad illumination spectrum at an angle substantially tangential to the surface of the eye; an optical collector configured for detecting reflected light from the at least a portion of the anterior region of the eye; an analyzer configured for analyzing the detected reflected light; and a processor configured to determine the analyte concentration level in the subject based on the analyzed reflected light, wherein the processor determines a hydration status of the subject based on the analyte concentration level and reference data.

19 Claims, 6 Drawing Sheets

OTHER PUBLICATIONS

Gaasterland et al., *Rhesus monkey aqueous humor composition and a primate ocular perfusate*; Invest. Ophthalmol. Visual Sci., Nov. 1979, pp. 1139-1150.

Davson et al., *The Effect of Acetazoleamide on the Chemical Composition of the Aqueous Humour and Cerebrospinal Fluid or Some Mammalian Species and on the Rate of Turnover of $^{24}NA$ in These Fluids*, Journal of Physiology, 1957, 18 pages.

Madsen et al., "Optical Filter Design and Analysis: A Signal processing Approach", (*Digital Filter Concepts for Optical Filters*), pp. 95-165, Oct. 2001.

International Search Report dated Mar. 30, 2010 issued in application No. PCT/US2010/022900, 2 pages.

Written Opinion of the International Searching Authority, dated Mar. 30, 2010 issued in application No. PCT/US2010/022900, 6 pages.

\* cited by examiner

METHOD AND SYSTEM FOR MONITORING HYDRATION

FIELD OF THE INVENTION

The disclosure relates generally to ocular diagnosis, and, more particularly, to a non-invasive method and device for determining health condition of a subject through measurements of concentrations of analytes in the eye.

BACKGROUND

The Blood-Aqueous Barrier ("BAB") is a metabolic or cellular structure in the anterior chamber of the eye ("ACE") that restricts the passage of various chemical substances and microscopic objects, such as bacteria, between the bloodstream and the ACE tissue itself, while still allowing the passage of substances essential to metabolic function, such as oxygen, sodium and potassium salts and glucose. During duress, which may include traumatic injury, radiation exposure or diseases, such as cancer, the normal function of the BAB is adversely affected and results in a range of typically locally blocked analytes crossing into the anterior chamber of the eye. As such, detection of such analytes in the human eye can be a reliable indicator of a person's health.

In addition to monitoring the analytes that cross the BAB during injury or disease, the monitoring of analytes that cross the BAB during normal conditions may also indicate the health condition of a subject. For example, a sufficiently hydrated person typically has a specific concentration range of sodium salts (natremia), and the ability to detect raised or lowered concentrations of these sodium salts may provide a reliable indication of a person's hydration level. On the one hand, some of the methods typically used for accurately determining the hydration status, such as Total Body Water ("TBW") measurements and invasive measurements of plasma osmolality, are complex and require a clinical setting.

On the other hand, some of the more rapid and non-invasive techniques, such as bioimpedence measurements made through the skin using weak electrical currents, salivary osmolality measurements (for hydration), and monitoring physical signs of dehydration or diabetes, require baseline characterizations and may not be very specific. Additionally, non-invasive measurement modalities that require electromagnetic/optic probing made through the skin are easily corrupted by skin temperature, perspiration and body position of the subject, therefore limiting their application. Further, many of the non-invasive methods measure the concentration of analytes in the eye using laser assisted measurements of absorption at a select few wavelengths.

SUMMARY

One illustrative embodiment of the disclosure provides a device for accurately measuring an analyte concentration level in the aqueous humour by spectroscopic analysis of the reflected/scattered light using a broadband continuous wavelength visible light source (200 nm to 900 nm). Herein, a radiation source illuminates an anterior region of the eye of the subject with a substantially broad spectrum at an angle substantially tangent to the eye. The reflected and scattered radiations are collected and analyzed to obtain a characteristic spectrum of the detected scattered and reflected radiations. The characteristic spectrum is a combination of the light absorbed and scattered by the analyte based on its refractive index, size of the analyte, natural optical absorption, as well as its optical activity. This characteristic spectrum is then compared with a reference characteristic spectrum to compute the analyte concentration. Illumination at a tangential angle may avoid the total internal reflection characteristics of the eye and enable light collection normal to the corneal surface. Analysis with a broad illumination spectrum enables the determination of the optical properties of the analyte over a large response region.

An optical collector is configured for detecting an amount of scattered and reflected radiations from the anterior region. An analyzer is configured for analyzing the detected scattered and reflected radiations obtained, and a processor is configured for comparing the characteristic spectrum of the detected scattered and reflected radiations with a reference characteristic spectrum to compute the analyte concentration.

In various embodiments of the disclosure, split-beam polarization analysis of optical activity in the aqueous humour using incoherent illumination is performed with substantially the same optical source/receiver arrangement, but with the addition of polarization measuring optical components to quickly and accurately measure an optically active analyte.

In one embodiment of the present invention, the analyte concentration is measured by a non-invasive method using optical reflection spectroscopy. Here, measurements are rapid since the method is passive and the analyte is not excited optically with a coherent or monochromatic source. This method is reliable for diagnosis and does not require any baseline measurement. In addition, a broad illumination spectrum primarily in the visible light range is used and hence the device is cost effective, and easy to operate.

An embodiment of the present invention provides a device for measuring a hydration status based on an analyte concentration level in a subject, the device including: a light source configured for illuminating at least a portion of an anterior region of an eye of the subject with incident light having a substantially broad illumination spectrum at an angle substantially tangential to the surface of the eye; an optical collector configured for detecting reflected light from the at least a portion of the anterior region of the eye; an analyzer configured for analyzing the detected reflected light; and a processor configured to determine the analyte concentration level in the subject based on the analyzed reflected light, wherein the processor determines a hydration status of the subject based on the analyte concentration level and reference data.

The reference data may correspond to a hydration level in an anterior region of a healthy eye.

The illumination spectrum may include wavelengths ranging from about 200 nm to about 900 nm.

The angle at which the eye is illuminated may range from about 70 degrees to about 90 degrees.

The device may further include a modulator configured for modulating the incident light to reduce extraneous effects.

The analyzer may include an optical spectrometer or an interferometer.

The light source may include an incoherent light source.

The analyte concentration level may include a Na concentration level.

Another embodiment of the present invention provides a method for measuring a hydration status based on an analyte concentration in a subject, the method including the steps of: irradiating at least a portion of an anterior region of an eye with incident light with a substantially broad illumination spectrum at an angle substantially tangential to the surface of the eye; detecting reflected light from the at least a portion of the anterior region; analyzing the reflected light; determining the analyte concentration level based on the analyzed reflected light; and determining a hydration status of the subject based on the analyte concentration level and reference data.

The method may further include modulating the incident light to reduce extraneous effects.

BRIEF DESCRIPTION OF THE DRAWINGS

Various embodiments of the invention will hereinafter be described in conjunction with the appended drawings provided to illustrate and not to limit the invention, wherein like designations denote like elements, and in which:

FIG. 1b illustrates the ray paths from the device in an eye according to FIG. 1a;

DETAILED DESCRIPTION

The detailed description set forth below in connection with the drawings is intended as a description of embodiments of a non-invasive method and device for determining health condition of a subject through measurements of concentrations of analytes in the eye in accordance with the present invention and is not intended to represent the only forms in which the invention may be constructed or utilized. It is to be understood that the same or equivalent functions and structures may be accomplished by different embodiments that are also intended to be encompassed within the spirit and scope of the invention. As denoted elsewhere herein, like element numbers indicate like elements or features.

An embodiment of the present invention provides a device and a method for non-invasively measuring concentration of an analyte in the human eye.

More specifically, an embodiment of the present invention provides a device for accurately measuring an analyte concentration level in the aqueous humor in the ACE by spectroscopic analysis of the reflected (or scattered) light using a broadband continuous wavelength illumination source (or a substantially broad illumination source). For example, the illumination source may have an illumination spectrum from about 200 nm to about 900 nm. Here, the illumination source illuminates the ACE (or anterior region of the eye) of the subject with light at an angle substantially tangent to the eye. It should be appreciated that the anterior region for purposes of the present disclosure is defined generally as is the region between the pupil and the cornea that encompasses the aqueous humor. The reflected light is collected and analyzed to obtain a reflected spectrum of the detected reflected light. This reflected spectrum is then compared with a reference spectrum to determine the analyte concentration.

The reference spectrum is prepared by in-vivo analysis. For example, reference spectra may be determined for different colored eyes or taking into account other physical parameters, such as corneal thickness.

Illumination at the tangential angle may substantially avoid total internal reflection within the eye, entry of light into the posterior chamber of the eye leading to substantial loss of light, and potential damage to the retinal region. Further, tangential illumination enables light collection normal to the corneal surface.

Figure 1A:
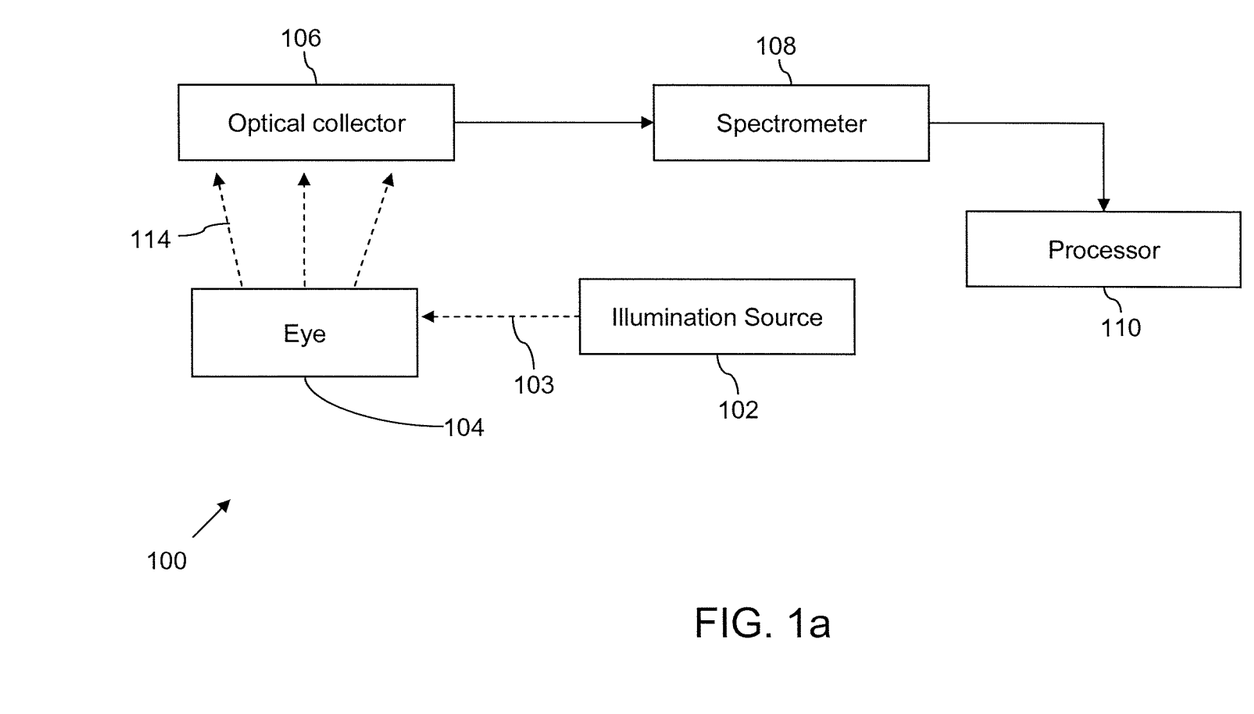
FIG. 1a illustrates a block diagram of a device for measuring analyte concentration level according to an embodiment of the present disclosure.

A device 100 for measuring at least one analyte concentration level in a subject according to an embodiment of the present invention is shown in FIG. 1a. The device 100 includes an illumination source (or optical illuminator) 102 for illuminating the ACE 104, and an optical collector 106 communicatively coupled to a spectrometer 108 configured for performing spectral analysis of the reflected light 114 from the eye 104. The device 100 also includes a processor 110 in communication with the spectrometer 108 and configured for determining the analyte concentration level.

The optical collector 106 can be coupled to the spectrometer 108 by using a data link, such as a fiber optic link. It should be appreciated that the optical collector 106 can be coupled to the spectrometer 108 by any other wired or wireless communication channels known to persons skilled in the art. Similarly, the spectrometer 108 can be communicatively coupled with the processor 110 with a wired or a wireless connection.

A standard illumination source may be a uniform visible light source with a halogen lamp, such as an ophthalmic slit lamp. A standard spectrometer may be a 2 nm grating or similar optically dispersive element, including holograms, coupled with a photodetector, such as a pixelated CCD array or photodiode array.

Figure 1B:
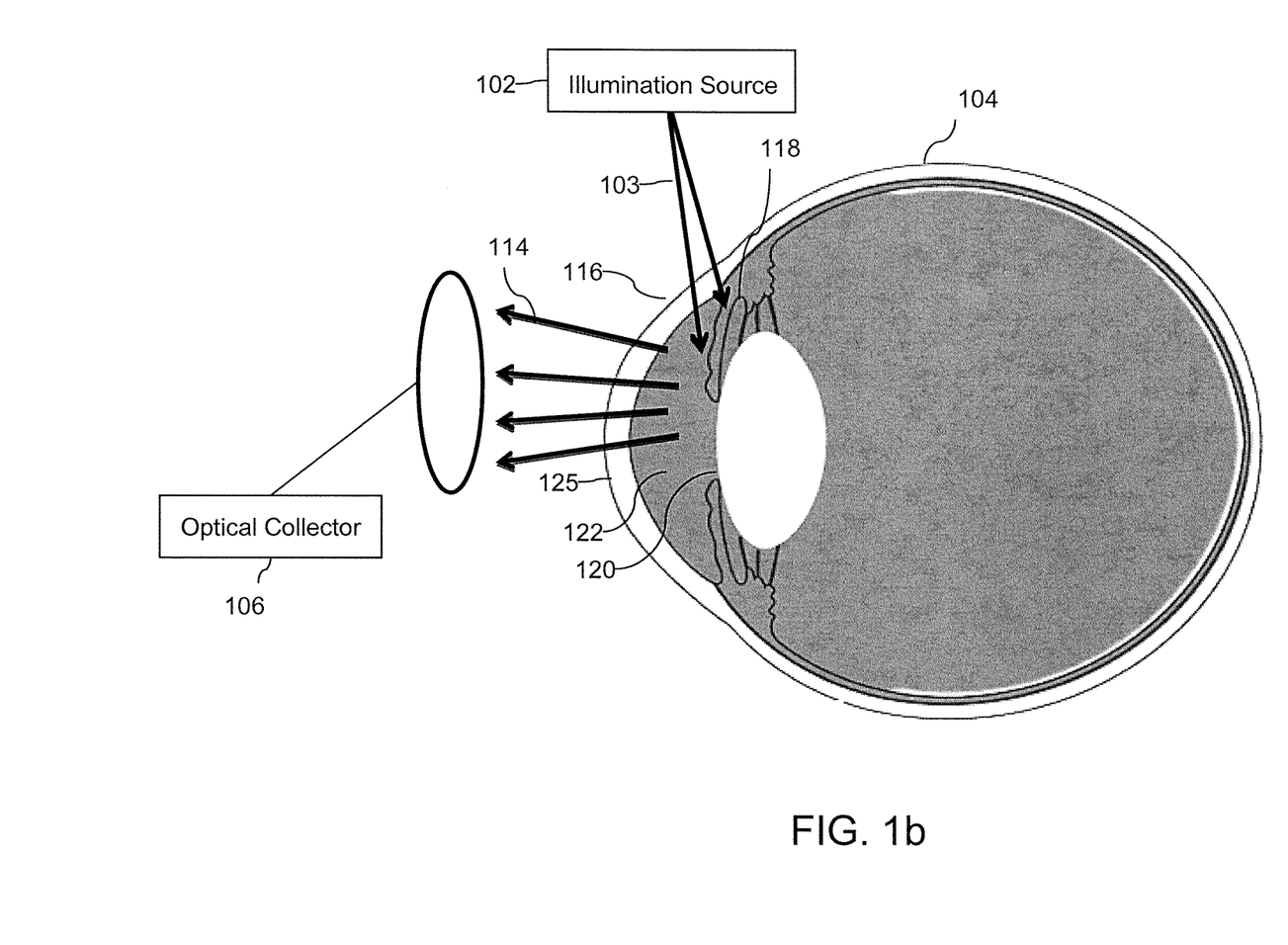
Figure 2:
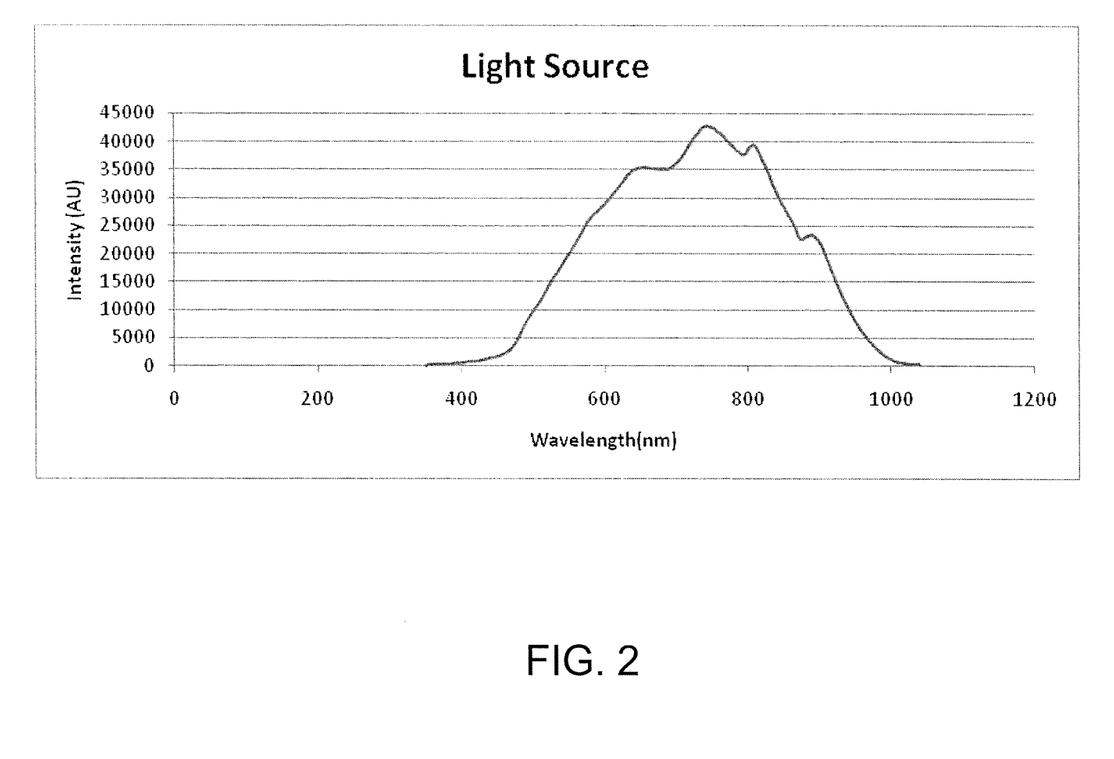
FIG. 2 is a graph that illustrates an illumination spectrum according an embodiment of the present disclosure.

As illustrated in FIG. 1b, the eye 104 can be illuminated by the illumination source 102, such that incident light 103 is directed at an angle tangential to the eye 104. In one embodiment, the incident light 103 is shaped with a combination of lenses such that it has a generally rectangular collimated profile.

The incident light 103 enters the cornea 116 and reflects off the iris 118. Therefore, a minimal amount of light enters the pupil 120. This increases the likelihood that only an anterior chamber 122 of the eye 104 is illuminated and the incident light 103 has a maximal path length in the anterior chamber 122 of the eye 104 where it traverses the aqueous humor in the anterior chamber 122.

The reflected light 114 from the anterior chamber 122 of the eye 104 is then collected by the optical collector 106 and further analyzed by the spectrometer 108 and processor 110 to determine the concentration of the analyte. It should be appreciated that reflected light 114 is collected from uniform illumination of the anterior chamber 122.

The reflected light 114 from the eye 104 is collected by the optical collector 106, for example, a collimating lens assembly. An example of a collimating lens includes the 74-DA Collimating Lens that consists of a single aspheric lens with a field-of-view (FOV) ~45°.

The spectrometer 108 performs an analysis, e.g., a spectral analysis, of the collected reflected light 114. For example, the spectrometer 108 may determine a reflected spectrum. The spectrometer 108 may, for example, be an optical spectrometer or an interferometer. The spectrometer 108 converts the reflected spectrum into electrical signals, which are analyzed by the processor 110. For example, the processor 110 may compare the reflected spectrum to a reference spectrum to determine an analyte concentration level in the aqueous humor.

Figure 5:
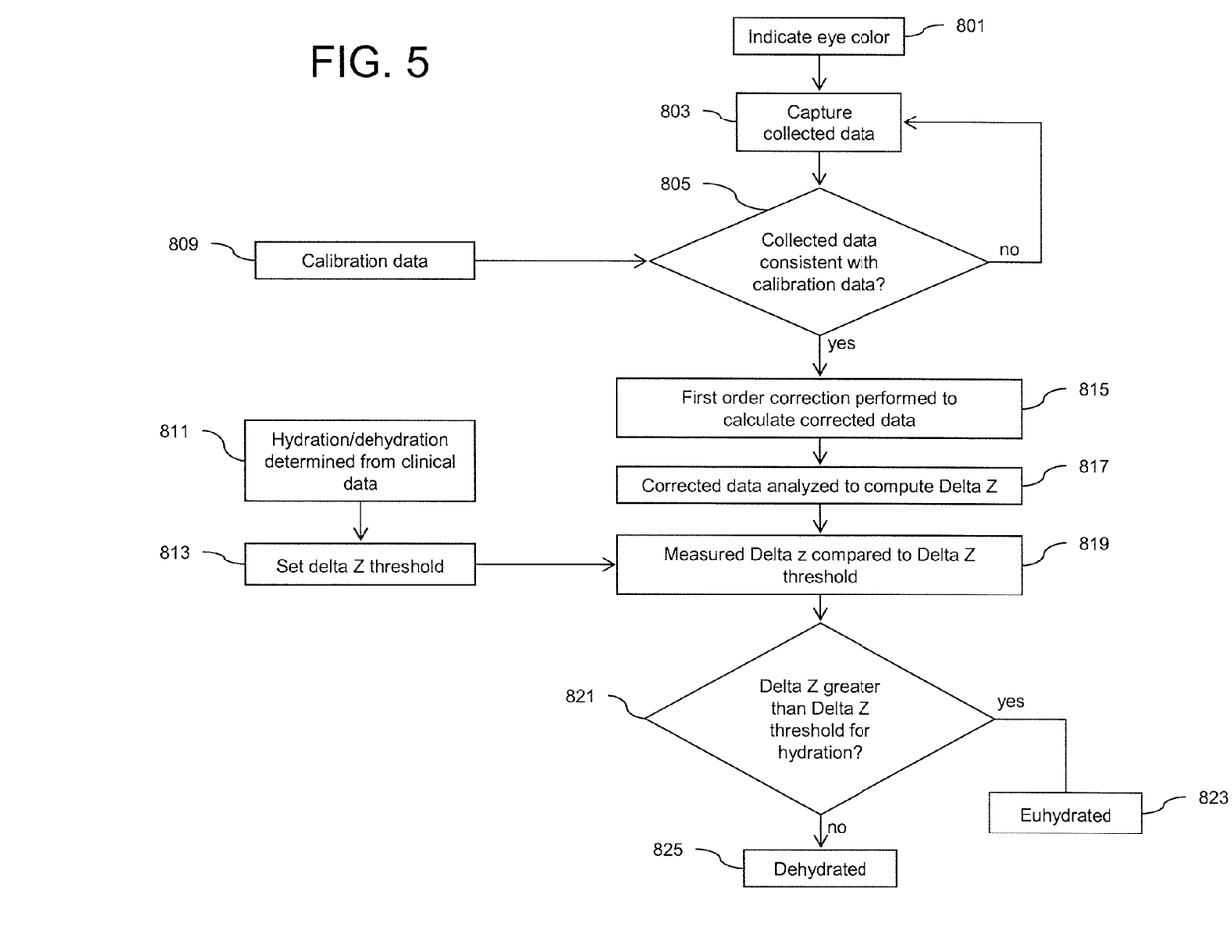
FIG. 5 is a flowchart illustrating a method for analyzing data to determine the hydration status of a subject according to an embodiment of the present invention.

An algorithm used to determine hydration status of a patient according to an embodiment of the present is illustrated in FIG. 5. Here, the user selects the approximate eye color of the test subject 801 based on broad color definitions, e.g., blue, green, brown or other similar categorization of the color of the iris. The reflected light 114 is captured 803 by the optical collector 106, analyzed by the spectrometer 108, and recorded by the processor 110 as collected data.

Calibration (or reference) data 809, including typical characteristics of light from the light source 103 that has been reflected from different colored irises, is stored in memory of the processor 110. Illumination source data, including the spectrum of the illumination source 102, is also stored in the memory of the processor 110. This calibration data may be parameterized values that include one or more spectral peaks, spectral full-width-at-half-maxima (FWHM), and spectral intensity.

The collected data is compared with the calibration data 805. If the collected data is not consistent with the calibration data, then the collected data is captured again. If the collected data is consistent with the calibration data, the processor 110 selects calibration data for further analysis that is consistent with the reflected light 114 coming from the iris 118, i.e., the iris of the selected color. Here, extraneous light from other regions of the eye, such as the sclera, pupil and eyelid, is rejected.

The collected data is further processed by performing a first order correction 815, where the calibration data and illumination source data are subtracted from the collected data. The resulting corrected data may, for example, be analyzed in the spectral region of 400 nm to 500 nm to compute a maximum deviation, Delta Z, from the calibration data 817. Data from clinical and laboratory experiments that empirically determines which values of Delta Z correspond to adequate hydration and which values of Delta Z correspond to dehydration are also stored in the processor. A Delta Z threshold for hydration, where values of Delta Z less than the Delta Z threshold correspond to dehydration and values of Delta Z greater than the Delta Z threshold correspond to euhydration (or adequate hydration), is compared with the computed Delta Z 821 to determine whether the Delta Z value is greater than the threshold for hydration 821. If the Delta Z value is less than the Delta Z threshold, then the subject is dehydrated or likely to be dehydrated 825. If the Delta Z value is greater than the Delta Z threshold, then the subject is adequately hydrated or likely to be adequately hydrated 823.

The reference spectrum and calibration data is obtained by performing a number of experiments and computing the concentration of different analytes in the eye using data obtained through measurements performed in clinical settings of humans and non-human primates subject to controlled and correlated variations of various analytes. Additional reference spectra that account for eye color, corneal thickness, and physical parameters of the eye that vary from individual to individual are also included. The reference spectra are stored in a memory unit in the processor 110.

Figure 3:
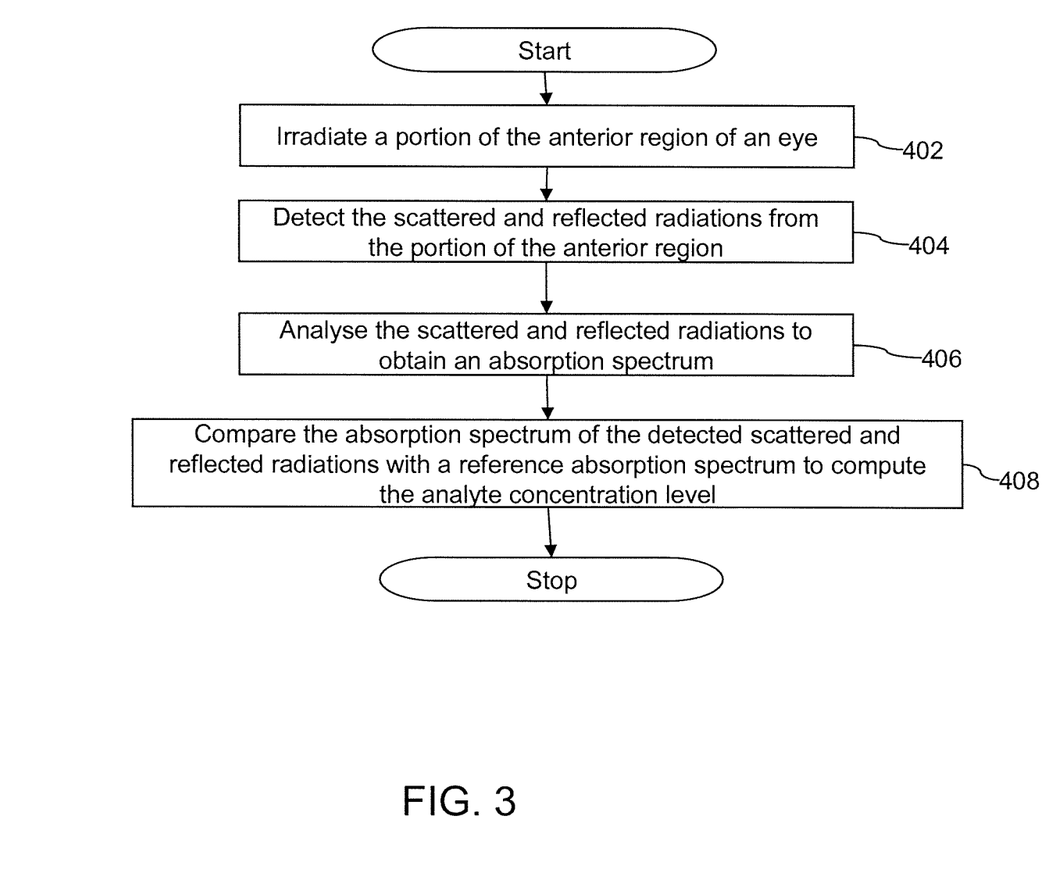
FIG. 3 is a flowchart illustrating a method for measuring an analyte concentration level in a subject according to an embodiment of the present disclosure.
Figure 4:
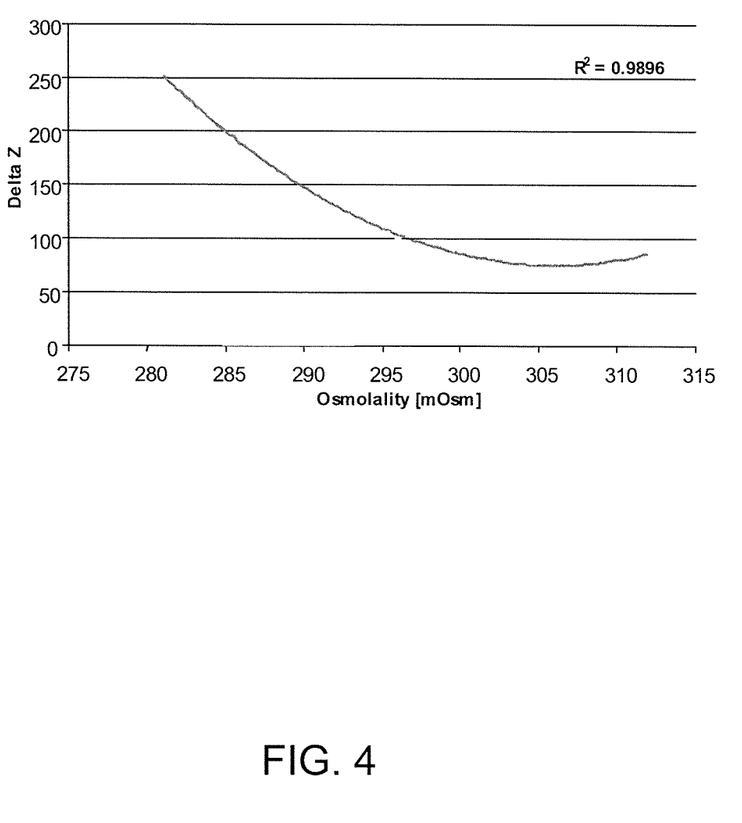
FIG. 4 is a graph of data from the device of FIG. 1 processed to determine aqueous humor osmolality.

In one embodiment, the illumination source 102 is a broadband continuous wavelength visible source that generates light having wavelengths in the range from about 200 nm to about 900 nm, and more specifically from about 300 nm to about 900 nm. It should be appreciated that the illumination source 102 can be an incoherent source and can generate non-polarized light. It should further be appreciated that the incident light may not be collimated. FIG. 3 is a graph illustrating an exemplary spectrum of the light generated by the illumination source. As illustrated, the wavelengths are in the range of about 300 nm to about 1000 nm.

In one embodiment of the present invention as shown in FIG. 1a, optical density of the aqueous humor is measured by reflection spectroscopy. FIG. 5 shows data that demonstrates a strong correlation between optical density of the aqueous humor obtained through the practice of the invention with corresponding osmolality changes of the aqueous humor. Measurements of osmolality are correlated to the amount of sodium (Na) based salts present in the human body. Lower values of Delta Z indicate lower levels of hydration.

According to another embodiment of the present invention, modulators such as frequency modulators and phase modulators can be used along with spectrometer 108 and processor 110 to reduce extraneous effects. By modulating the illumination source, e.g., in phase and/or time, and synchronizing the measurement of the reflected light at the spectrometer, effects from noise, such as ambient light and intrinsic fluorescence, can be mitigated. Here, the source is modulated, and the receiver is synchronized to respond to a carrier wave represented by the modulation. The carrier wave modulation is then removed at the detector to extract the useful signal. Similarly, optical filters can be used with the optical collector 106 or illumination source 102 to filter and/or block radiation from extraneous sources.

FIG. 3 is a flowchart illustrating a method for measuring an analyte concentration level in a subject according to an embodiment of the present invention. At step 402, the anterior portion of an eye similar to eye 104 is illuminated at a tangential angle by a light source similar to light source 102. According to another embodiment of the invention, the angle at which the eye is illuminated is in the range of about 70 degrees to about 90 degrees.

At step 404, the reflected and scattered rays are captured by an optical collector similar to optical collector 106. Optical collector 106 is coupled to a spectrometer similar to spectrometer 108. At step 406, reflected and scattered light is analyzed by the spectrometer to obtain a characteristic spectrum. The spectrometer is connected to a processor similar to processor 110. At step 408, the processor compares the characteristic spectrum of the detected scattered and reflected radiations with a reference characteristic spectrum to compute the analyte concentration level. The comparison is performed using multivariable analysis and calibration techniques. The multivariate calibration techniques may include Classical Least Square (CLS), Inverse Least Square (ILS), Principal Component (PC) and Partial Least Square (PLS).

The present disclosure measures the analyte concentration using a non-invasive method using optical reflection spectroscopy and optical absorption. The present invention is rapid as the method is passive and analyte is not excited optically. This method may be reliable for diagnosis and does not require any baseline measurements. In addition, a broad spectrum primarily in the visible light range is used and hence the device is cost effective, and easy to operate. Further, the system or device can be integrated with an eyewear such a spectacles or sunglasses.

Although the present invention has been described through the use of exemplary embodiments, it will be appreciated by those of skill in the art that various modifications may be made to the described embodiments that fall within the scope and spirit of the invention as defined by the claims and their equivalents appended hereto.

What is claimed is:

1. A device for measuring a hydration status based on an analyte concentration level in a subject, the device comprising:
   a light source configured for illuminating at least a portion of an anterior region of an eye of the subject with incident light having a substantially broad illumination spectrum at an angle substantially tangential to the surface of the eye;

an optical collector configured for detecting at least one of scattered or reflected light from the at least a portion of the anterior region of the eye;

an analyzer configured for analyzing the detected at least one of scattered or reflected light; and a processor configured to determine the analyte concentration level in the subject based on the analyzed at least one of scattered or reflected light, wherein the processor determines a hydration status of the subject based on the analyte concentration level and reference data.

2. The device of claim 1, wherein the reference data corresponds to a hydration level in an anterior region of a healthy eye.

3. The device of claim 1, wherein the illumination spectrum comprises wavelengths ranging from about 200 nm to about 900 nm.

4. The device of claim 1, wherein the angle at which the eye is illuminated ranges from about 70 degrees to about 90 degrees.

5. The device of claim 1, further comprising a modulator configured for modulating the incident light to reduce extraneous effects.

6. The device of claim 1, wherein the analyzer comprises an optical spectrometer.

7. The device of claim 1, wherein the analyzer comprises an interferometer.

8. The device of claim 1, wherein the light source comprises an incoherent light source.

9. The device of claim 1, wherein the analyte concentration level comprises a Na concentration level.

10. A method for measuring a hydration status based on an analyte concentration in a subject, the method comprising the steps of:

irradiating at least a portion of an anterior region of an eye with incident light with a substantially broad illumination spectrum at an angle substantially tangential to the surface of the eye;

detecting at least one of scattered or reflected light from the at least a portion of the anterior region;

analyzing the at least one of scattered or reflected light;

determining the analyte concentration level based on the analyzed at least one of scattered or reflected light; and determining a hydration status of the subject based on the analyte concentration level and reference data.

11. The method of claim 10, wherein the reference data corresponds to analyte concentration levels in the anterior chamber of a healthy eye.

12. The method of claim 10, wherein the illumination spectrum comprises wavelengths ranging from about 200 nm to about 900 nm.

13. The method of claim 10, further comprising modulating the incident light to reduce extraneous effects.

14. The method of claim 10, wherein the analyzing the at least one of scattered or reflected light comprises analyzing the at least one of scattered or reflected light with an optical spectrometer.

15. The method of claim 10, wherein the analyzing the at least one of scattered or reflected light comprises analyzing the at least one of scattered or reflected light with an interferometer.

16. The method of claim 10, wherein the incident light comprises incoherent light.

17. The method of claim 10, wherein the illumination spectrum comprises wavelengths ranging from about 200 nm to about 900 nm.

18. The method of claim 10, wherein the angle at which the eye is illuminated ranges from about 70 degrees to about 90 degrees.

19. The method of claim 10, wherein the analyte concentration level comprises a Na concentration level.

* * * * *